United States Patent [19]

Dötz

[11] 4,374,775

[45] Feb. 22, 1983

[54] PROCESS FOR PREPARING VITAMIN K

[75] Inventor: Karl H. Dötz, Vaterstetten, Fed. Rep. of Germany

[73] Assignee: Hoffmann-La Roche Inc., Nutley, N.J.

[21] Appl. No.: 319,355

[22] Filed: Nov. 9, 1981

Related U.S. Application Data

[62] Division of Ser. No. 127,002, Mar. 4, 1980, Pat. No. 4,320,065.

[30] Foreign Application Priority Data

Mar. 8, 1979 [DE] Fed. Rep. of Germany ....... 2909091
Jan. 15, 1980 [CH] Switzerland ........................... 306/80

[51] Int. Cl.³ .............................................. C07C 97/18
[52] U.S. Cl. .......................... 260/396 K; 26/438.5 R; 260/396 R

[58] Field of Search ................... 260/438.5 R, 396 R, 260/396 K

[56] References Cited

U.S. PATENT DOCUMENTS 3,444,224, 5/1969 Whiting ........................... 260/438.5
4,089,873 5/1978 Rapport et al. ................ 260/396 K
4,320,065 3/1982 Dotz .......................... 260/396 K X Primary Examiner—Robert V. Hines
Attorney, Agent, or Firm—Jon S. Saxe; George M. Gould; William H. Epstein

[57] ABSTRACT

A process for preparing vitamins of the vitamin $K_1$ and $K_2$ series in their E-isomeric form through the reaction of a phenylcarbene metal complex with an enyne and intermediates in this synthesis.

3 Claims, No Drawings

PROCESS FOR PREPARING VITAMIN K

This is a division of application Ser. No. 127,002 filed Mar. 4, 1980 now U.S. Pat. No. 4,320,065.

BACKGROUND OF THE INVENTION

Vitamin $K_1$ having the formula:

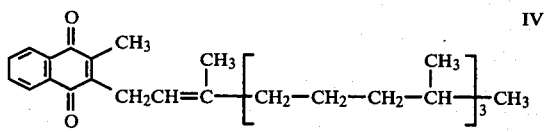

and vitamins of the vitamin $K_2$ series having the formula

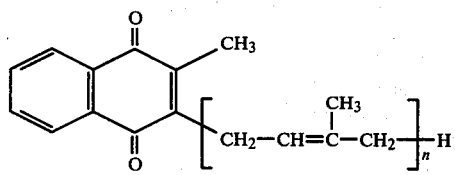

where n is an integer of from 1 to 13 are known in part as natural substances. These vitamin K series of compounds are used as additives for feedstuffs, for investigations metabolism and other purposes. These compounds can be present, with reference to the first double-bond (viewed from the naphthoquinone ring) in the terpene chain, in Z-form (also called cis-form) or in E-form (also called trans-form) or as a mixture of these two forms. In biological investigations, the Z-form has proved to be biologically less active, if not even inactive. In the case of vitamin K, a "lack of biological activity" was ascertained for the cis-form in J. Nutr. 105:1519–1524, 1975. According to O. Isler in Angew. Chem., 71 (1959) No. 1., pages 13–15, in the case of substances of the vitamin $K_1$ and $K_2$ series, the mono-cis compounds (cis double-bond adjacent to the naphtoquinone ring system) showed a significantly lower activity than the all trans forms.

The efforts towards synthetic production of substances of the vitamin $K_1$ and $K_2$ series—the K vitamins influence the biosynthesis of prothrombin and other blood-coagulation factors—were indeed soon succesful. Thus, a process for the manufacture of vitamin $K_{1(20)}$ starting from a methylnaphthohydroquinone and the corresponding terpene alcohol with a subsequent oxidation step was already described in 1939. There was obtained a total yield of 29%, based on phytol, without disclosing the E/Z ratios in the compounds obtained.

Recent processes, as disclosed e.g. in U.S. Pat. No. 2,683,176 or in German patent application 2,733,233, start from corresponding methyl-substituted naphthohydroquinone monoether derivatives, which are reacted with the corresponding terpene alchols or terpene ethers and the resulting reaction products are oxidized. While in the former process there is obtained e.g. a yield of vitamin $K_1$ of 37.5%, based on phytol, with a E/Z ratio of 90 to 92.5/7.5 to 10, the latter process leads only to the E-isomeric form with good yields of vitamin $K_1$.

In other processes, methylnaphthohydroquinone and the respective terpene derivatives are condensed in the presence of metals such as zinc amalgam or zinc dust. In this case, the product is obtained in low total yields with the formation of E/Z-isomer mixtures. The use of N-sulphinylamines as the condensation agent has also been described, whereby, based on phytol, yields of vitamin $K_1$ of only 4 to 7% have been obtained, but in the form of the pure E-isomers.

There exits thus a need for the provision of a process for the manufacture of compounds of the vitamin $K_1$ and vitamin $K_2$ series, in which these compounds are obtained in high yield and in a relatively simple manner. Since the synthesis of the specific methyl-substituted naphthohydroquinone derivative is expensive, the discovery of such processes in which this starting material need not be employed has been desired. In this case, it is especially desirable that such processes lead stereospecifically to the exclusively or predominantly biologically active E-form.

SUMMARY OF THE INVENTION

In accordance with this invention, a process is provided for producing vitamins of the $K_1$ and $K_2$ series (i.e. compounds of formula IV-A and IV-B) by reacting a phenyl-carbene-carbonyl metal complex of the formula

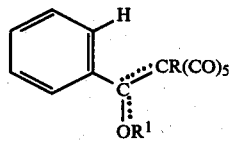

wherein $R^1$ is lower alkyl, acyl or benzyl, with an enyne of the general formula

wherein $R^2$ is dimethylallyl, geranyl, farnesyl, or an analogous isoprenoid terpenyl residue or the phytyl residue; to produce a naphthol-carbonyl-metal complex of the formula:

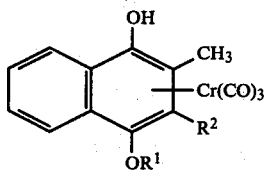

wherein $R^1$ and $R^2$ are as above. The naphthol-carbonyl-metal complex of formula III is converted to the compound of formula:

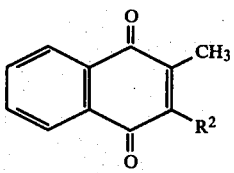

wherein $R_2$ is as above, by cleaving the metal-ring bond, i.e. $-Cr(CO)_3$ in the compound of formula III. In certain cases, cleaving may not directly produce the compound of formula IV but rather produces the corresponding naphthol derivative. If this is the case, the naphthol derivative is oxidized to the compound of formula IV.

By this process, the desired compounds of the vitamin $K_1$ or $K_2$ series are produced. The particular vitamin $K_1$ and $K_2$ compound produced dpends on the nature of the substituent $R^2$. Furthermore, this process is extremely advantageous since it has been surprisingly discovered that the compounds of formula IV are produced having the E-configuration, when the enyne of formula II has an E-configuration.

Therefore, this invention provides a process for the stereospecific synthesis of compounds of the vitamin $K_1$ and $K_2$ series. Through this synthesis, these compounds can be produced specifically in the E-form in high yields. Furthermore, the process of this invention provides a simple and efficient means for producing compounds of the vitamin K series in only a few steps with the simple intermediate formation of the naphthol ring.

DETAILED DESCRIPTION OF THE INVENTION

"Aryl" designates mononuclear aromatic hydrocarbon groups such as phenyl, ect., which can be unsubstituted or substituted in one or more positions with a lower alkyl substitutent and polynuclear aryl groups such as naphthyl, anthryl, phenanthryl, azulyl, etc., which can be unsubstituted or substituted with one or more of the aforementioned lower alkyl groups. The preferred aryl groups are the substituted and unsubstituted mononuclear aryl groups, particularly phenyl.

Throughout the present specification, the term "lower alkyl" means particularly alkyl groups with 1-7 carbon atoms such as methyl, ethyl, isopropyl and the like, the methyl radical being preferred. The term "acyl" stands for particularly lower alkanoyl groups with up to 7 carbon atoms such as acetyl, propionyl, butyryl and the like, as well as for aroyl groups where aryl is defined as above. Among the preferred aroyl substituents are included benzoyl and the like.

The term "analogous isoprenoid terpenyl residue" includes such residues as

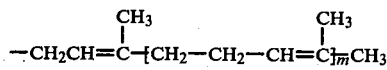

wherein m is an integer of from 3 to 13.

In the complex of formula I, the dotted bond indicates a partial double bond. The complex of formula I designates a structure which is a resonance hybrid between the compound of formula I having a carbon to oxygen double bond and the compound of formula I having a carbon to chromium double bond.

The phenyl-carbene-carbonyl-metal complexes of formula I used as starting materials in the present process are known compounds or analogous to known compounds. These compounds can be prepared according to Darensbourg et., Inorg. Chem. 9, 32 (1970). For the purpose of the present invention, the pentacarbonyl (methoxy-phenylcarbene)chromium complex as well as the pentacarbonyl(acetoxyphenylcarbene)chromium complex are particularly preferred. All the above complexes are compounds which under nitrogen and low temperature are extremely stable.

The enynes of the general formula II used as the further reaction partner are partly known and partly new compounds. The new compounds can be prepared in an analogous manner to the preparation of the known compound and are also part of the present invention. For example the 5-methyl-4-hexen-1-yne or the 6-methyl-5-hepten-2-yne are known compounds and the new compounds, i.e. geranyl, farnesyl and phytyl derivatives, respectively, viz. 6.10-dimethyl-5.9-undecadien-2-yne; 6.10.14-trimethyl-5.9.13-pentadecatrien-2-yne and 6.10.14.18-tetramethyl-5-nonadecen-2-yne can readily be synthesized in an analogous manner. In this case one generally starts from propynylmagnesium bromide in ether and slowly adds dropwise thereto a solution of the respective terpene halide, especially terpene bromide R-Br (R=geranyl, farnesyl, phytyl) in ether. After heating under reflux for several hours, the mixture is poured onto ice and optionally diluted acid (e.g. acetic acid) and extracted with an organic solvent. After washing and usual working-up, there is then obtained the desired enyne as a crude product in good yield.

The reaction of an enyne of formula II (in the case of the use thereof in the E-form) with a metal-carbene complex of formula I leads in a one-step, rapidly proceeding reaction directly and stereospecifically to the E-type of the in each case desired vitamin K product in the hydroquinoid form of formula III, which can then with retention of the desired E-form, be transformed to the desired end product of formula IV.

In the process in accordance with the present invention the reaction of the carbene complex of formula I with the enyne of formula II is usually carried out under protective gas atmosphere, e.g. under nitrogen, argon, etc. However, an oxygen-admittance can also be avoided by any other suitable method.

In carrying out this reaction, any conventional organic donor solvent can be used as the reaction medium, with ethers being especially preferred. In this case, there can be employed with advantage high-boiling ethers, e.g. ter.butyl methy ether or dibutyl ether, the reaction then proceeding conveniently at elevated temperature.

In carrying out this reaction, temperature is not critical. Although the reaction proceeds at room temperature, it is preferred to carry out the reaction e.g. at a temperature in the range between about 25° and 80° C. and preferably between about 50° and about 60° C. The reaction proceeds well and completely with stoichiometric ratios of the reaction partners, whereby the substituted naphtholtricarbonyl-chromium complexes result in yields of at least 85% up to 100% of theory. Preferably, however, the enyne is employed in a slightly over-stoichiometric ratio, over the starting carbene compound, for example 1,1:1=enyne: starting carbene complex. However, if desired, any ratio of starting materials can be utilized.

The naphthol-tricarbonyl-chromium complexes of formula III are novel compounds and form also part of the present invention.

The cleaving of the metal-ring bond in the compounds of formula III can be carried out in different ways. Thus, this cleaving can for instance be carried out using an oxidizing agent, in which case the oxidation of the naphthol derivative to the compounds of formula IV occurs simultaneously. In carrying out this reaction, any conventional oxidizing agent can be utilized. Any of the conditions conventional in using these oxidizing agents can be utilized in this conversion. This reaction can be carried out directly following the formation of the substituted naphthol-carbonyl-metal complex of formula III in a one-pot process or also after isolation of the complex of formula III and purification thereof, insofar as this appears to be convenient.

Among the preferred oxidizing agents is included the oxidizing agent silver oxide. The use of silver oxide leaves the terpene substituent intact but is capable of cleaving the metal-ring bond and can convert the hydroquinone compound readily into the quinoid end product. In the oxidative cleavage of the metal-ring bond with Ag$_2$O there can result, in addition to the desired quinone, also a small amount (e.g. 5%) of the quinone-Cr(CO)$_3$ complex of the formula

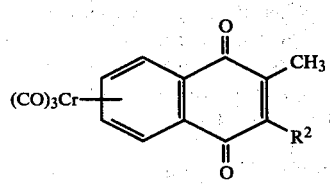

wherein R$^2$ has the above meanings.

The occurrence of this undesirable by-product can, however, be prevented by the use of stronger oxidation agenst such as e.g. H$_2$O$_2$, MnO$_2$, PbO$_2$ or NiO$_2$. It is therefore preferred in many embodiments of the invention to carry out this reaction, for example, with 20% H$_2$O$_2$, e.g. in a non-polar solvent at room temperature.

If the oxidation is carried out directly after the formation of the complex of formula III, without isolation thereof, the oxidation can be carried out conveniently with silver (I) oxide in the presence of MgSO$_4$ or other water-entraining agents.

Furthermore, the cleaving of the metal-ring bond in the compounds of the formula III can in principle also be carried out with all such reagents with which usually a lower oxidation level of transition elements can be stabilized. As examples of such reagents there can be named: carbon monoxide, which is prefereably used under pressure, particularly under a pressure of from about 50 to about 100 atmospheres, phosphines, e.g. triphenylphosphine, phosphites, e.g. trimethylphosphite, isonitriles, olefines, e.g. cyclooctadiene or norbornadiene, aromatic compounds such as benzene, methyl or halogen substituted benzene, benzoic acid esters, aniline or alkyl derivatives thereof or nitrogen bases such as pyridine and the like. In using these agents, any of the conditions conventionally used can be used in this process step.

In case the cleavage of the metal-ring bond is not carried out with an oxidation agent but with one of the foregoing mentioned agents, the then obtained naphthol derivative still has to be oxidized to the compounds of the general formula IV. This oxidation can be carried out according to methods known per se, for example with silver oxide or also with air.

The chromium carbonyl obtained according to the non-oxidative cleavage of the metal-ring bond can, if desired, after treatment with carbon monoxide, be recycled in the process in the form of chromium-hexacarbonyl.

The particulars of the process of the present invention are shown on the basis of the following working directions for the manufacture of the enynes, insofar as they are not prior known, the manufacture of the complex of formula III as well as the cleavage of the metal-ring bond and the oxidation step which leads to the end products of formula IV.

EXAMPLE 1

Manufacture of the enynes of formula II

A spatula tip of copper (I) chloride is added to a solution of 30 mmol of propynylmagnesium bromide in 20 ml of ether and subsequently a solution of 30 mmol of R-Br (R=geranyl, farnesyl, phytyl) in 20 ml of ether is added slowly. After twelve-hours heating under reflux, the mixture is poured into ice and dilute acetic acid and extracted with ether. The mixture is washed neutral with dilute sodium hydroxide and water and dried over MgSO$_4$. After the removal of the solvent, there is obtained the enyne as a crude product in 65 to 85% yield.

Trans-(10R,14R)-6,10,14,18-tetramethyl-5-nonadecen-2-yne: b.p. 131°-145° C./0,15 mmHg

EXAMPLE 2

Preparation of the compounds of forumula III 1 mmol of carbonyl-carbene-chromium complex is heated at 25° to 80° C. while stirring with 1,1 mmol of enyne in 5 ml of a donor solvent under protective gas (N$_2$) during ½ to 3 hours. After chromatography over silica gel with methylene chloride/pentane mixtures, there are obtained the substituted naphthol-tricarbonyl-chromium complexes in yields of 85 to 100%.

EXAMPLE 3

Cleavage of the metal-ring bond and simultaneous oxidation of the resulting naphthol derivatives (here after previous isolation of the obtained complexes of formula III)

The 2.3.4-trisubstituted 1-naphthol-tricarbonyl-chromium complex obtained from 1 mmol of carbonyl-carbene-chromium complex and 1,1 mmol of crude enyne is oxidised in ether with an excess of Ag$_2$O. The chromatographical working-up on silica gel with pentane/ether mixtures at −10° to 20° C. yields 30% to 50% of 2.3-disubstituted naphthoquinone.

The batch can be increased proportionally.

EXAMPLE 4

Cleavage of the metal-ring bond with carbon monoxide

The 2.3.4-trisubstituted 1-naphthol-tricarbonyl-chromium complex obtained from 1 mmol of carbonyl-carbene-chromium complex and 1,1 mmol of crude enyne is heated in ether in a steel autoclave under a carbon monoxide pressure of about 50 to 100 atmospheres to a temperature of about 60° to about 100° C. After opening of the autoclave, the solution is filtered, the solvent is evaporated from the filtrate and the residue is chromatographed. There is obtained the desired naphthol derivative which afterwards can be transformed to the end product of formula IV by oxidation.

The working conditions set forth in the above examples can be correspondingly altered, since they only represent a preferred embodiment of the invention which is not to be understood as limiting.

Hereinafter there is now to be described the manufacture of vitamin K$_{1(20)}$.

EXAMPLE 5

Manufacture of vitamin K$_1$

A solution of 1 mmol of pentacarbonyl[methoxy(-phenyl)carbene]chromium and 1,1 mmol of 6.10.14.18-tetramethyl-5-nonadecen-2-yne from phytyl bromide (isomer ratio (E/Z=90/10) in 5 ml of dibutyl ether is heated to 55° C. under nitrogen for 1 hour. After the removal of the solvent, the 1-naphthol-tricarbonyl-chromium complex can be isolated (yield 95%) by chromatography on silica gel at −30° C. with methylene chloride/pentane (2/1), or directly oxidised to the quinone after addition of 10 ml of ether by one-hours stirring with 1,5 mmol of silver (I) oxide in the presence of MgSO4. The obtained mixture is filtered, the solvent removed and the residue purified by chromatography at 10° C. on silica gel with pentane/ether (100/1). There is obtained vitamin $K_{1(20)}$ as a light yellow oil in a total yield of 56%.

Isomer ratio E/Z=87:13 (±5) ($^1$H-NMR spectroscopic determination).

The observed isomer ratio E/Z was already present (within the limits of error) in the starting enyne, whereby the proof of a strictly sterospecific course of the described addition reaction is furnished.

The end products obtained were identified by IR, NMR spectra as well as mass-spectroscopic investigations by comparison with known spectra. Also, the purity determinations as well as the establishment of the E/Z-isomer ratios were carried out on the basis of the $^1$H-NMR spectroscopy and the CH analysis.

Hereinafter there are given for compounds of the $K_1$ and $K_2$ series the analysis values obtained as well as the isomer ratios E/Z as follows.

biologically active substances of the vitamin $K_1$ or $K_2$ series in the E-form.

EXAMPLE 6

A solution of 340 mg of the tricarbonyl-(4-methoxy-2,3-methyl-phytyl-1-naphthol)chromium complex (prepared according to Example 5) in 35 ml of ether is heated in a 100 ml steel autoclave at a temperature of 80° C. during 6 hours under a carbon monoxide pressure of 85 at. After opening of the autoclave, the yellow solution is filtered and cooled to −40° C. Thereby the majority of the formed chromium hexacarbonyl precipitates and can be filtered off. After elimination of the solvent, there remains an orange colored oil, which for further purification is chromatographed on silica gel. The so obtained naphthol derivative can be oxidised to vitamin $K_{1(20)}$ in known manner.

I claim:

1. The process of producing a compound of the formula

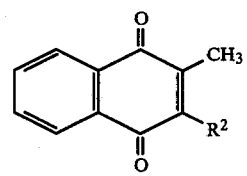

IV

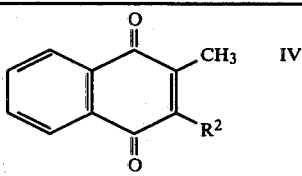

IV

|  | E/Z | Analysis values | | Yield (based on R—Br) |
|---|---|---|---|---|
| $R^2$ = dimethylallyl | — | calc.: C 79.97 | H 6.71 | 51% |
|  |  | found: C 80.42 | H 7.35 |  |
| $R^2$ = geranyl ($K_{2(10)}$) | 85:15 | calc.: C 81.78 | H 7.84 | 54% |
|  |  | found: C 81.47 | H 8.20 |  |
| $R^2$ = farnesyl ($K_{2(15)}$) | 85:15 | calc.: C 82.93 | H 8.57 | 55% |
|  |  | found: C 82.88 | H 8.97 |  |
| $R^2$ = phytyl ($K_{1(20)}$) | 87:13 | calc.: C 82.61 | H 10.29 | 56% |
|  |  | found: C 82.29 | H 10.63 |  |

The above values indicate the high yield obtained. The yields are based on highly pure product and were not optimised. At the same time, it is evident that the reaction proceeds strictly stereospecifically having regard to the exclusive formation of the desired biologically active form. This was verified in that the chosen E/Z ratio of the enyne used (geranyl bromide, farnesyl bromide and phytyl bromide with a E/Z ratio of 85:15, 85:15 and 87:13) remains preserved in the end product of the synthesis. With the use of the uniform E-forms of the enynes there thus result exclusively the desired wherein $R^2$ is dimethylallyl, geranyl, farnesyl or an analogous isoprenoid terpenyl residue or the phytyl residue comprising oxidizing a compound of the formula:

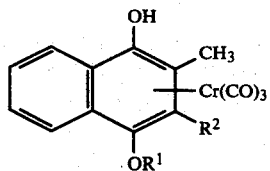

wherein $R^1$ is lower alkyl, acyl or benzyl and $R^2$ is as above with an oxidizing agent.

2. The process of claim 1 wherein silver oxide is the oxidizing agent.

3. The process of claim 1 wherein $H_2O_2$, $MnO_2$ or $NiO_2$ is the oxidizing agent.

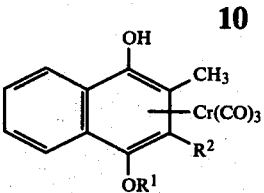

wherein $R^1$ is lower alkyl, acyl or benzyl and $R^2$ is as above with an oxidizing agent.

2. The process of claim 1 wherein silver oxide is the oxidizing agent.

3. The process of claim 1 wherein $H_2O_2$, $MnO_2$ or $NiO_2$ is the oxidizing agent.

* * * * *